United States Patent [19]
Hingott et al.

[11] Patent Number: 6,093,839
[45] Date of Patent: Jul. 25, 2000

[54] PROCESS FOR THE PREPARATION OF ACYLGLUTAMATE SOLUTIONS

[75] Inventors: Thomas Hingott, Kriftel; Joachim Hess, Hofheim, both of Germany

[73] Assignee: Clariant GmbH, Frankfurt, Germany

[21] Appl. No.: 09/251,827

[22] Filed: Feb. 17, 1999

[30] Foreign Application Priority Data

Feb. 17, 1998 [DE] Germany ................. 19806512

[51] Int. Cl.$^7$ .................................. C07C 231/00
[52] U.S. Cl. ................. 554/69; 554/68; 560/155
[58] Field of Search .................. 554/68, 69; 560/155

[56] References Cited

U.S. PATENT DOCUMENTS 3,758,525   9/1973   Yoshida et al. .

FOREIGN PATENT DOCUMENTS 1082179   9/1967   Germany .

Primary Examiner—Deborah D. Carr
Attorney, Agent, or Firm—Miles B. Dearth

[57] ABSTRACT

Process for the preparation of acylglutamate solutions by reaction of a glutamic acid salt with an acid chloride in water and in the presence of an anionic or zwitterionic surfactant.

5 Claims, No Drawings

PROCESS FOR THE PREPARATION OF ACYLGLUTAMATE SOLUTIONS

FIELD OF THE INVENTION

Acylglutamates are a type of mild surfactant and are notable for very good biodegradability, low aquatic toxicity and mild, good to excellent skin and mucosa tolerability. Acylglutamates are used widely as care components, particularly sodium cocoylglutamate in cosmetic cleansing preparations.

The synthesis of acylglutamates is based on the known Schotten-Baumann reaction, i.e. the reaction of fatty acid chlorides with the amino group of sodium glutamate.

In order to react the lipophilic fatty acid chloride with the hydrophilic amino acid or the parent salt in an aqueous medium, the earlier procedures require the addition of an organic solvent, such as, for example, acetone, methyl ethyl ketone, dioxane, tetrahydrofuran, tert-butanol or cyclohexane (U.S. Pat. No. 3,758,525). A disadvantage of this process is the fact that the organic solvent must be removed from the reaction mixture in processes that are very time-consuming and costly.

The object of the present invention is to find a process for the preparation of acylglutamates which does not require solvents.

SUMMARY OF THE INVENTION

Surprisingly, it has been found that by adding surfactants to the aqueous reaction mixture, it is possible to dispense with an organic solvent. The presence of a surfactant enables the concentration of the acylglutamate reaction product in the finished aqueous solution to be increased to from 25 to 40% by weight, in particular from 25 to 35% by weight.

The invention thus provides a process for the preparation of acylglutamates of the formula

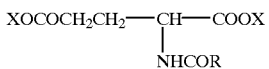

in which R is $C_6$–$C_{36}$-alkyl, preferably $C_{10}$–$C_{18}$-alkyl or $C_6$–$C_{36}$-alkenyl, preferably $C_{10}$–$C_{18}$-alkenyl and X is an alkali metal ion or ammonium ion, by reaction of a glutamic acid salt of the formula

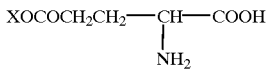

with an acid chloride of the formula

in water and in the presence of an anionic or zwitterionic surfactant.

The process is preferably carried out by firstly preparing an approximately 10 to 30% strength aqueous glutamate solution and adding the surfactant and alkali metal hydroxide. The amount of surfactant is such that the finished acylglutamate solution generally comprises from 2 to 50% by weight, preferably from 3 to 30% by weight, in particular from 5 to 25% by weight, of surfactant. The amount of alkali is from 1.0 to 1.03 mol of alkali per mole of glutamic acid salt. This solution is cooled to from about 10 to 20° C., and then the equimolar amount of fatty acid chloride is slowly added thereto. At the same time, enough alkali metal hydroxide is added in order to keep the reaction mixture at a pH of from about 12.2 to 12.6. In the process, the temperature should not exceed 10 to 20° C. After the fatty acid chloride has been added, the reaction mixture is then stirred for about a further 2 hours without cooling and its pH is then adjusted to from 9 to 10.

DESCRIPTION OF THE PREFERRED EMBODIMENTS

Suitable surfactants are all anionic and zwitterionic surfactants which do not react with the acid chloride and which are resistant to alkali.

In very general terms, anionic surfactants which may be used are alkyl-sulfates, alkylsulfonates, alkylcarboxylates, alkylphosphates, and mixtures thereof. The anionic surfactants which are suitable for the present invention are water-soluble or can be dispersed in water. These anionic surfactants comprise, as cation, sodium, potassium, calcium, magnesium, ammonium or substituted ammonium cations, including mono-, di- or triethanolammonium cations.

Particularly suitable surfactants are alkylsulfates of the formula $ROSO_3M$, in which R is $C_{10}$–$C_{14}$-alkyl, preferably $C_{10}$–$C_{20}$-alkyl, in particular $C_{12}$–$C_{18}$-alkyl and M is hydrogen or a cation, for example an alkali metal cation (e.g. sodium, potassium or lithium) or ammonium or substituted ammonium, for example methyl-, dimethyl- and trimethylammonium cations and quaternary ammonium cations, such as tetramethylammonium and dimethylpiperidinium cations.

Surfactants which are particularly suitable for the novel process are water-soluble alkyl ether sulfates c)f the formula $RO(A)_mSO_3M$, in which R is a $C_{10}$–$C_{24}$-alkyl, preferably $C_{12}$–$C_{20}$-alkyl, particularly preferably $C_{12}$–$C_{18}$-alkyl. A is an ethoxy or propoxy unit, m is greater than 0, typically a number between about 0.5 and about 6, particularly preferably between about 0.5 and about 3 and M is hydrogen or a cation, such as, for example, a metal cation (e.g. sodium, potassium, lithium, calcium, magnesium, etc.), ammonium or a substituted ammonium cation. Specific examples of substituted ammonium cations are methyl-, dimethyl-, trimethylammonium and quaternary ammonium cations, such as tetramethylammonium and dimethylpiperidinium cations. Examples which may be mentioned are $C_{12}$–$C_{18}$-alkylpolyethoxysulfates containing in each case 1, 2.25, 3 or 4 moles of ethylene oxide and sodium or potassium as the cation.

Another suitable anionic surfactant which may be used according to the invention is alkylbenzenesulfonate. The alkyl group can be either saturated or unsaturated, and branched or linear. Preferred alkylbenzenesulfonates contain linear alkyl chains having from 9 to 25 carbon atoms, preferably from 10 to 13 carbon atoms; the cation is sodium, potassium, ammonium, mono-, di- or triethanolammonium, calcium or magnesium and mixtures thereof.

It is likewise possible to use secondary alkanesulfonates, in which case the alkyl group can be either saturated or unsaturated, branched or linear. The sulfo group is randomly distributed over the whole carbon chain, the primary methyl groups at the start of the chain and at the end of the chain having no sulfonate group. Preferred secondary alkanesulfonates contain linear alkyl chains having from 9 to 25 carbon atoms, preferably having from 10 to 20 carbon atoms and particularly preferably having from 13 to 17 carbon atoms. The cation is sodium, potassium, ammonium, mono-, di- or triethanolammonium, calcium or magnesium and mixtures thereof. For the sake of simplicity, sodium is the preferred cation.

Other surfactants which can be used are carboxylates, for example fatty acid soaps. The soaps can be saturated or unsaturated and can contain various substituents, for example alpha-sulfonate groups. They preferably contain linear saturated or unsaturated hydrocarbon radicals as the hydrophobic component. The hydrophobic components usually contain from 6 to 30 carbon atoms, preferably from 10 to 18 carbon atoms. The cation is an alkali metal cation, for example sodium or potassium, an alkaline earth metal cation, for example calcium or magnesium, or ammonium or substituted ammonium including mono-, di- and triethanolammonium.

Other anionic surfactants are salts of acylaminocarboxylic acids which are formed in the reaction of fatty acid chlorides with sodium sarcosinate in an alkaline medium (acyl sarcosinates), and the salts of alkylsulfamidocarboxylic acids and the salts of alkyl and alkylaryl ether carboxylic acids. It is likewise possible to use the acylglutamates themselves as surfactants in the novel process.

Other anionic surfactants which may be used are $C_8$–$C_{24}$-olefinsulfonates, sulfonated polycarboxylic acids prepared by sulfonation of the pyrrolysis products of alkaline earth metal citrates, as is described, for example, in GB-A-1 082 179, alkyl glycerol sulfates, fatty acyl glycerol sulfates, oleyl glycerol sulfates, alkylphenol ether sulfates, primary paraffinsulfonates, alkylphosphates, alkyl ether phosphates, isethionates, such as acylisethionates, N-acyltaurides, alkylsuccinamates, sulfosuccinates, monoesters of sulfosuccinates (particularly saturated and unsaturated $C_{12}$–$C_{18}$ monoesters) and diesters of sulfosuccinates (particularly saturated and unsaturated $C_{12}$–$C_{18}$-diesters), sulfates of alkylpolysaccharides and alkylpolyethoxycarboxylates, such as those of the formula $RO(CH_2CH_2)_kCH_2COO—M^+$ in which R is a $C_8$–$C_{22}$-alkyl, k is a number from 0 to 10 and M is a cation which forms a soluble salt. Resin acids or hydrogenated resin acids, such as rosin or tall oil resins and tall oil resin acids can also be used.

Zwitterionic surfactants which can be used in the novel process are, in quite general terms, aliphatic secondary or tertiary amines having a linear or branched $C_8$–$C_{18}$-alkyl radical and which contain an anionic, water-soluble group, such as, for example, a carboxyl, sulfonate, sulfate, phosphate or phosphonate group.

Typical examples of zwitterionic surfactants are alkylbetaines, alkylamidobetaines, aminopropionates, aminoglycinates or amphoteric compounds of the formula $$R^1CONR^4(CH_2)_nN^\oplus R^2R^3CH_2ZX^\ominus$$

in which $R^1$ is $C_8$–$C_{22}$-alkyl or -alkenyl, $R^2$ is hydrogen or $CH_2CO_2M$, $R^3$ is $CH_2CH_2OH$ or $CH_2CH_2OCH_2COOM$, $R^4$ is hydrogen, $CH_2CH_2OH$ or $CH_2CH_2COOM$, Z is $CO_2M$ or $CH_2CO_2M$, n is 2 or 3, preferably 2, M is hydrogen or a cation, such as alkali metal, alkaline earth metal, ammonia or alkanolammonium.

Preferred zwitterionic surfactants of this formula are monocarboxylates and dicarboxylates. Examples thereof are cocoamphocarboxypropionate, cocoamidocarboxypropionic acid, cocoamphocarboxyglycinate (also referred to as cocoamphodiacetate) and cocoamphoacetate.

Further preferred zwitterionic surfactants are alkyldimethylbetaines and alkyldipolyethoxybetaines containing an alkyl radical which may be linear or branched having from about 8 to about 22 carbon atoms, preferably having from 8 to 18 carbon atoms and particularly preferably having from about 12 to about 18 carbon atoms. These compounds are marketed, for example by Clariant AG under the trade name ®Genagen LAB.

Of all the abovementioned surfactants, the acylglutamates, in particular cocoylglutamate, alkyl ether sulfate, in particular lauryl ether sulfate, and alkylamidopropylbetaines, in particular cocoamidopropylbetaine, are preferred. It is also preferable to use a mixture of different surfactants.

EXAMPLE 1

Preparation of Disodium $C_{12}$-acylglutamate 440 g of water, 196.7 g of monosodium glutamate, 128.5 g of 33% strength sodium hydroxide solution and 102.5 g of ®Genapol LRO (liquid) are cooled to from 10 to 20° C. in a reactor which has been rendered inert using $N_2$. In the course of 8 hours, 245.9 g of lauryl fatty acid chloride and simultaneously from 120 g to 130 g of 33% strength sodium hydroxide solution are added dropwise using a metering pump. Throughout the reaction period, the pH must be maintained at from 12.2 to 12.6. In addition, the temperature of the reaction mixture during the metering phase must be between 10 and 20° C. In the subsequent stirring period (about 2 h) NaOH is added to adjust the pH to a value between 11.0 and 12.0. Cooling to from 10 to 20° C. is no longer necessary in the subsequent stirring period. At the end of the subsequent stirring period, the reaction product is heated to 60° C. and adjusted to a pH of from 9 to 10 using hydrochloric acid.

EXAMPLE 2

Preparation of Disodium $C_{12}$–$C_{18}$-cocoylglutamate 440 g of water, 196.7 g of monosodium glutamate, 128.5 g of 33% strength sodium hydroxide solution and 102.5 g of ®Genapol LRO (liquid) are cooled to from 10 to 20° C. in a reactor which has been rendered inert using $N_2$. In the course of 8 hours, 252.3 g of coconut fatty acid chloride and simultaneously from 120 g to 130 g of 33% strength sodium hydroxide solution are added dropwise using a metering pump. Throughout the reaction period, the pH must be maintained at from 12.2 to 12.6. In addition, the temperature of the reaction mixture during the metering phase must be between 10 and 20° C. In the subsequent stirring period (about 2 h) NaOH is added to adjust the pH to a value between 11.0 and 12.0. At the end of the subsequent stirring period, the reaction product is heated to 60° C. and adjusted to a pH of from 9 to 10 using hydrochloric acid.

EXAMPLE 3

Preparation of Disodium $C_{12}$–$C_{18}$-cocoylglutamate 440 g of water, 196.7 g of monosodium glutamate, 128.5 g of 33% strength sodium hydroxide solution and 120.4 g of ®Hostapon KCG are cooled to from 10 to 20° C. in a reactor which has been rendered inert using $N_2$. In the course of 8 hours, 252.3 g of $C_{12}$–$C_{18}$-coconut fatty acid chloride and simultaneously from 120 g to 130 g of 33% strength sodium hydroxide solution are added dropwise using a metering pump. Throughout the reaction period, the pH must be maintained at from 12.2 to 12.6. In addition, the temperature of the reaction mixture during the metering phase must be between 10 and 20° C. In the subsequent stirring period (about 2 h) NaOH is added to adjust the pH to a value between 11.0 and 12.0. At the end of the subsequent stirring period, the reaction product is heated to 60° C. and adjusted to a pH of from 9 to 10 using hydrochloric acid.

EXAMPLE 4

Preparation of Disodium $C_{10}$-acylglutamate 440 g of water, 196.7 g of monosodium glutamate, 128.5 g of 33% strength sodium hydroxide solution and 115.5 g of ®Genagen CAB are cooled to from 10 to 20° C. in a reactor which has been rendered inert using $N_2$. In the course of 8 hours, 216.3 g of decanoyl chloride and simultaneously from 120 g to 130 g of 33% strength sodium hydroxide solution are added dropwise using a metering pump. Throughout the reaction period, the pH must be maintained at from 12.2 to 12.6. In addition, the temperature of the reaction mixture during the metering phase must be between 10 and 20° C. In the subsequent stirring period (about 2 h) NaOH is added to adjust the pH to a value between 11.0 and 12.0. At the end of the subsequent stirring period, the reaction product is heated to 60° C. and adjusted to a pH of from 9 to 10 using hydrochloric acid.

EXAMPLE 5

Preparation of Disodium $C_{12}$–$C_{14}$-cocoylglutamate 440 g of water, 196.7 g of monosodium glutamate, 128.5 g of 33% strength sodium hydroxide solution and 102.5 g of Genapol LRO, liquid are cooled to from 10 to 20° C. in a reactor which has been rendered inert using $N_2$. In the course of 8 hours, 249.5 g of $C_{12}$–$C_{14}$-coconut fatty acid chloride and simultaneously from 120 g to 130 g of 33% strength sodium hydroxide solution are added dropwise using a metering pump. Throughout the reaction period, the pH must be maintained at from 12.2 to 12.6. In addition, the temperature of the reaction mixture during the metering phase must be between 10 and 20° C. In the subsequent stirring period (about 2 h) NaOH is added to set a pH between 11.0 and 12.0. At the end of the subsequent stirring period, the reaction product is heated to 60° C. and adjusted to a pH of from 9 to 10 using hydrochloric acid.

Chemical names of the tradenames

| Genapol LRO, liquid | 27.0% of a sodium $C_{12}$–$C_{14}$-alkyldiglycol ether sulfate in water, Clariant GmbH |
|---|---|
| Hostapon KCG | 25% of monosodium acylglutamate in water, Clariant GmbH |
| Genagen CAB | 30% of cocoamidopropylbetaine, Clariant GmbH |

We claim:

1. A process for the preparation of acylglutamates of the formula

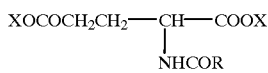

in which R is $C_6$–$C_{35}$-alkyl or $C_6$–$C_{36}$-alkenyl and X is an alkali metal ion or ammonium ion, by reaction of a glutamic acid salt of the formula

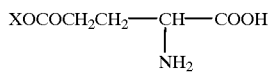

with an acid chloride of the formula

which comprises carrying out the reaction in water and in the presence of an anionic or zwitterionic surfactant.

2. The process as claimed in claim 1, wherein the reaction is carried out in the presence of from 2 to 50% by weight of surfactant.

3. The process as claimed in claim 1, wherein the reaction is carried out in the presence of an acylglutamate, alkyl ether sulfate and/or alkylamidopropylbetaine.

4. The process as claimed in claim 2, wherein said reaction is carried out with from 3 to 30% of said surfactant.

5. The process as claimed in claim 4, wherein said reaction is carried out with from 5 to 25% of said surfactant.

* * * * *